United States Patent [19]

Kosinski

[11] Patent Number: 4,961,728
[45] Date of Patent: Oct. 9, 1990

[54] SINGLE-USE SYRINGE HAVING MISUSE RESISTANT FEATURES

[75] Inventor: Anthony J. Kosinski, New Providence, N.J.

[73] Assignee: Becton, Dickinson and Company, Franklin Lakes, N.J.

[21] Appl. No.: 292,277

[22] Filed: Dec. 30, 1988

[51] Int. Cl.$^5$ .............................................. A61M 5/00
[52] U.S. Cl. ..................................... 604/110; 604/238
[58] Field of Search ............... 604/110, 220, 218, 236, 604/238

[56] References Cited

U.S. PATENT DOCUMENTS

| | | | |
|---|---|---|---|
| 1,496,654 | 6/1924 | Crowther | 604/220 |
| 2,216,354 | 10/1940 | Pletcher | 604/220 |
| 3,890,971 | 6/1975 | Leeson et al. | 604/110 |
| 4,367,738 | 1/1983 | Legendre et al. | 128/218 |
| 4,386,606 | 6/1983 | Tretinyak et al. | 604/220 |
| 4,758,232 | 7/1988 | Chak | 604/220 |
| 4,781,683 | 11/1988 | Wozniak et al. | 604/110 |
| 4,781,684 | 11/1988 | Trenner | 604/110 |
| 4,840,616 | 6/1989 | Banks | 604/218 |

FOREIGN PATENT DOCUMENTS

89/02287  3/1989  World Int. Prop. O. .......... 604/110

Primary Examiner—C. Fred Rosenbaum
Assistant Examiner—Sharon Rose
Attorney, Agent, or Firm—John L. Voellmicke

[57] ABSTRACT

A syringe assembly includes a barrel having an inside surface describing a chamber for retaining fluid, an open proximal end and a distal barrel end having a passageway therethrough in fluid communication with the chamber. A plunger rod includes an elongate body portion, a proximal end and a distal end with a stopper at the distal end. The stopper is slidably positioned in fluid-tight engagement in the barrel. A locking element is positioned in the barrel between the plunger rod and the inside surface of the barrel. The locking element includes at least two proximally and outwardly facing non-parallel locking barbs, a distally and inwardly facing resisting edge and an inwardly facing driving edge. The driving edge is adaped to interact with the plunger rod to move the locking element along the barrel as the stopper is advanced distally along the barrel. The resisting edge and the locking barbs are adapted to prevent proximal motion of the plunger rod with respect to the barrel after initial distal motion of the plunger rod to expel fluid through the passageway wherein proximal motion of the plunger rod with respect to the barrel causes the resisting edge to engage the plunger rod causing the locking element to move in a proximal direction wherein the locking barbs engage the inside surface of the barrel to prevent further movement and allowing only distal movement of the plunger rod with respect to the barrel.

23 Claims, 5 Drawing Sheets

SINGLE-USE SYRINGE HAVING MISUSE RESISTANT FEATURES

BACKGROUND OF THE INVENTION

1. Field of the Invention.

The present invention relates to syringes and more particularly concerns disposable syringes having single use features.

2. Description of Related Information.

In the United States and throughout the world the multiple use of hypodermic syringe products which are intended for single use only is instrumental in drug abuse and more particularly in the transfer of contagious diseases. Intravenous drug users who routinely share and reuse syringes are a high risk group with respect to the AIDS virus. Also, the effects of multiple use are a major concern in third world countries where repeated use of syringe products may be responsible for the spread of many diseases. Reuse of single use hypodermic syringe assemblies is also instrumental in the spread of drug abuse even in the absence of infection or disease.

Many attempts have been made to remedy this problem. Most notable are early contributions which relied on a specific act to destroy the syringe after use either by using a destructive device or providing a syringe assembly with frangible zones so that the syringe could be rendered inoperable by the application of force. Other attempts involve the inclusion of structure which would allow the destruction or defeating of the syringe function through a conscious act by the syringe user. Although many of these devices work quite well they do require the specific intent of the user followed by the actual act to destroy or render the syringe inoperable. None of these devices is effective with a user having the specific intent to reuse the hypodermic syringe. Accordingly, there is a need for a single use hypodermic syringe which becomes inoperative or incapable of further use automatically without any additional act on the part of the user. This automatic function is much harder to provide because the means for rendering the syringe inoperable must not prevent its filling or use under normal conditions.

Along these lines, Legendre et al. U.S. Pat. No. 4,367,738 teaches a syringe having a barrel with a restricted open end which interacts with a plunger rod having a plurality of short flexible spikes attached at an oblique angle away from the piston. During injection, the oblique spikes will pass through the restricted opening in the barrel but the plunger rod motion in a reverse direction will be prevented by the oblique spikes. The syringe of Legendre et al. is suitable only for prefilled use because the plunger rod can not be fully withdrawn. The plunger rod of this syringe may be moved back and forth, as to reuse, for the distance between tips on the spike. For example, if the tips on adjacent spikes are one centimeter apart, when measured along the axis of the plunger rod the piston would appear to be cyclable back and forth for a distance slightly less than one centimeter. This syringe of Legendre et al. must have many spikes along the axis of the plunger rod to be rendered unreusable as a practical matter. A solution to the problem of multiple use which only addresses prefilled syringes is limited in nature because millions of injections each year are performed with vaccines that must be used a short time after being placed into injectable form by mixing with water.

Wozniak et al. U.S. Pat. No. 4,781,683 teaches a single use syringe that is rendered inoperative without requiring any deliberate action on the part of the user. Wozniak et al. accomplished this result by providing a hydrophilic expansion plug which is positioned in the outlet channel of the syringe which expands a short time after being exposed to a drug containing water to render the syringe inoperative. The syringe of Wozniak et al. may not function in a prefilled mode wherein the syringe is filled through the hypodermic needle because the syringe would probably be rendered inoperative before the time of use. Also, in many hospital applications, syringes are prefilled through the delivery tip in the hospital pharmacy and sent to the nursing stations for use immediately or during the next several hours or days. It would appear that the syringe of Wozniak et al. would not be applicable to this use because it would be rendered inoperative before time of use unless the hydrophilic expansion plug required an extended amount of time to reacts, and in this latter case it would not be a single use syringe.

Another single use hypodermic syringe is taught by Trenner in U.S. Pat. No. 4,781,684. Trenner appears to have overcome many of the shortcomings of the prior art with respect to the most common application of hypodermic syringes which is syringes being filled through the needle tip at the time of use or within a short period of time before use. The syringe of Trenner appears to allow for the easy filling and substantially unrestricted use. Trenner provides an annular groove near the distal end of the syringe barrel having a diameter which is greater than the diameter of the cylindrical inner surface of the barrel. A locking element, positioned between the stopper and the plunger rod, has an outside diameter which is larger than the diameter of the barrel so that when the syringe stopper is moved to its furthest most position inside the barrel, expelling medicament from the syringe, the locking element engages the annular groove and prevents withdrawal of the stopper. The design appears to allow for the forced disconnection of the plunger rod from the stopper while still retaining the stopper in the barrel. While the approach of Trenner overcomes many of the shortcomings of the prior art the Trenner syringe can be recycled many times so long as the user is careful not to move the stopper all the way to the distal end so as to engage the locking element with the annular groove.

SUMMARY OF THE INVENTION

An operable single use syringe assembly of the present invention includes a barrel having an inside surface describing a chamber for retaining fluid, an open barrel end, and a distal barrel end having a passageway therethrough in fluid communication with the chamber. A plunger rod having an elongate body portion, a proximal end and a distal end is provided. A stopper at the distal end of the plunger rod is slidably positioned in fluid tight engagement inside the barrel. A locking element is positioned in the barrel between the elongate body portion of the plunger rod and the inside surface of the barrel. The locking element includes a proximally and outwardly facing locking barb, a distally and inwardly facing resisting edge and an inwardly facing driving edge. The driving edge of the locking element is adapted to interact with the elongate body portion of the plunger rod to move the locking element along the barrel as the stopper is advanced along the barrel. The resisting edge and the barb are adapted to prevent proximal motion of the plunger rod with respect to the barrel after the initial distal motion of the stopper to expel fluid through said passageway wherein proximal motion of the plunger rod with respect to the barrel causes the resisting edge to engage the plunger rod causing the locking element to move in a proximal direction wherein the locking barb engages the inside surface of the barrel to prevent further proximal movement and allowing only distal movement of the plunger rod with respect to the barrel. Barrier means is provided on the elongate body portion of the plunger rod for limiting the delivery volume of the syringe assembly by establishing the maximum proximal position of the locking element with respect to the elongate body portion.

In accordance with another embodiment of the present invention, a syringe assembly having single use features includes a plastic barrel having an inside surface describing a chamber for retaining fluid, an open proximal end, and a distal barrel end having a passageway therethrough in fluid communication with the chamber. A plunger rod assembly includes a plunger rod having an elongate body portion including a longitudinal recess, a proximal end, and a distal end, and a stopper at the distal end. The stopper is slidably positioned in fluid tight engagement in the barrel so that the body portion extends outwardly from the open proximal end of the barrel. A metal locking element is positioned in the barrel between the longitudinal recess of the plunger rod and the inside surface of the barrel. The longitudinal recess of the plunger rod acts as a pathway for the longitudinal motion of the locking element relative to the elongate body portion. The element includes a proximal portion and a distal portion, a proximally and outwardly facing locking barb, a distally and inwardly facing resisting edge and an inwardly facing driving edge at the proximal portion of the element. The driving edge is adapted to interact with the longitudinal recess of the plunger rod to move the locking element along the barrel as the stopper is advanced distally along the barrel by force applied to the plunger rod. The resisting edge and the barb are adapted to prevent proximal motion of the plunger rod with respect to the barrel after initial distal motion of the stopper to expel fluid through the passageway wherein proximal motion of the plunger rod with respect to the barrel causes the resisting edge to engage the longitudinal recess causing the locking element to move in a proximal direction wherein the locking barb engages the inside surface of the barrel to prevent further movement and allowing only distal movement of the plunger rod with respect to the barrel. A barrier means is provided in the longitudinal recess for limiting the delivery volume of the syringe assembly by establishing the maximum proximal position of the locking element with respect to the elongate body portion.

Another embodiment of the present invention is a single-use syringe assembly having misuse resistant features including a barrel having an inside surface describing a chamber for retaining fluid, an open proximal end and a distal barrel end having a passageway therethrough in fluid communication with the chamber. A plunger rod includes an elongate body portion, a proximal end and a distal end. A stopper at the distal end of the plunger rod is slidably positioned in fluid tight engagement in the barrel. A locking element is positioned in the barrel between the elongate body portion of the plunger rod and the inside surface of the barrel. The locking element includes at least two proximally and outwardly facing non parallel locking barbs, a distally and inwardly facing resisting edge and an inwardly facing driving edge. The driving edge is adapted to interact with the body portion of the plunger rod to move the locking element along the barrel as the stopper is advanced distally along the barrel. The resisting edge and the locking barbs are adapted to prevent proximal motion of the plunger or with respect to the barrel after initial distal motion of the stopper to expel fluid through said passageway wherein proximal motion of the plunger rod with respect to the barrel causes the resisting edge to engage the plunger rod causing the locking element to move in a proximal direction wherein the locking barbs engage the inside surface of the barrel to prevent further movement and allowing only distal movement of the plunger rod with respect to the barrel.

Another embodiment of the single use syringe assembly having misuse resistant features includes a plastic barrel having an inside surface describing a chamber for retaining fluid, an open proximal end and a distal barrel end having a passageway therethrough in fluid communication with the chamber. A plunger rod assembly including a plunger rod having an elongate body portion including a longitudinal recess, a proximal end, and a distal end. A stopper at the distal end of the plunger rod is slidably positioned in fluid-tight engagement in the barrel wherein said elongate body portion of the plunger rod extends outwardly from the open proximal end of the barrel. A metal locking element is positioned in the barrel between the longitudinal recess of the plunger rod and the inside surface of the barrel. The elongate recess acts as a pathway for the longitudinal motion of the locking element relative to the elongate body portion. The element includes a proximal portion and a distal portion. The locking element further includes at least two proximally and outwardly facing non parallel locking barbs, a distally and inwardly facing resisting edge and an inwardly facing driving edge at the proximal portion of the element. The driving edge is adapted to interact with the longitudinal recess of the plunger rod to move the locking element along the barrel as the stopper is advanced distally along the barrel by force applied to the plunger rod. The resisting edge and the barbs are adapted to prevent proximal motion of the plunger rod with respect to the barrel after initial distal motion of the stopper to expel fluid through the passageway wherein subsequent proximal motion of the plunger rod with respect to the barrel causes the resisting edge to engage the longitudinal recess causing the locking element to move in a proximal direction wherein the locking barbs engage the inside surface of the barrel to prevent further movement and allowing only distal movement of the plunger rod with respect to the barrel. A tamper resistant barrier is located on the elongate body portion of the plunger rod proximally of the intended path of the locking element along the longitudinal recess to prevent undesirable access to the locking element.

DETAILED DESCRIPTION

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 10, a syringe assembly 20, having single use features, includes a barrel 21 having an inside surface 22 describing a chamber 23 for retaining fluid. Barrel 21 includes an open end 25 and a distal barrel end 27 having a passageway 28 therethrough in fluid communication with chamber 23. A needle cannula 29 having a sharpened distal tip 31 and a lumen therethrough in fluid communication with passageway 28 projects outwardly from distal barrel end 27. The syringe of the instant invention is preferably used with a cannula which is attached to the distal end of the syringe using adhesives or other suitable means. It will be apparent to one skilled in the art that the instant syringe may be used in applications not requiring a needle attached directly to the syringe such as with a removable needle and hub assembly or in other applications not requiring a needle where its single use features are desired, and that the attached cannula of the preferred embodiment is only one of these many possibilities.

For the purposes of the description of the present invention, the term "distal end" is meant to refer to the end furthest from the person holding the syringe, whereas the term "proximal end" is meant to refer to the end closest to the holder of the syringe.

A plunger assembly 32 includes a stopper 39 and a plunger rod 33 having an elongate body portion 34. The elongate body portion includes a longitudinal recess 35, a proximal end 37, and a distal end 38. In this preferred embodiment the longitudinal recess is v-shaped when viewed along the longitudinal axis of elongate body portion 34 with the narrowest portion of the recess being closes to the center of the elongate body portion. stopper 39 is positioned at distal end 38 of the plunger rod. The stopper is slidably positioned in fluid tight engagement in the barrel while a portion of body portion 34 of the plunger rod extends outwardly from open end 25 of the barrel. The plunger rod is accessible outside of open end 25 of the barrel and is provided to move the stopper along the barrel to force fluid into and out of the chamber 23 through passageway 28. Disc shaped plunger rod flange 40 is provided as a convenient structure for applying forces to move the plunger rod with respect to barrel 21. A flange 41 is also provided at the proximal end of the barrel to facilitate handling and positioning the syringe and for maintaining the relative position of the barrel with respect to the plunger rod during filling and medication administration.

It is within the purview of the present invention to include plunger rods and stoppers which are integrally formed of the same material or different materials, such as in two color molding, or separately formed of the same or different materials and joined together by mechanical means, adhesive, ultraonsonic welding, heat sealing or other suitable means. It is understood that the plunger rod assembly of this preferred embodiment is merely illustrative of these many possibilities.

A locking element 42 is positioned in the barrel and partially within longitudinal recess 35 between the plunger rod and the inside surface 22 of the barrel. Longitudinal recess 35 of the plunger rod acts as a pathway for longitudinal motion of the locking element relative to the elongate body portion of the plunger rod. Element 42 includes a proximal portion 44. Proximal portion 44 includes a proximally and outwardly facing locking barb 46. In addition proximal portion 44 also includes two additional anti twist locking barbs 47 and 49 which are preferably not facing in the same direction as locking barb 46. Locking barbs 47 and 49 are optional but important in helping prevent misuse of the instant syringe to overcome the single use function by twisting the plunger rod as will be explained in more detail hereinafter.

Figures 8, 9:
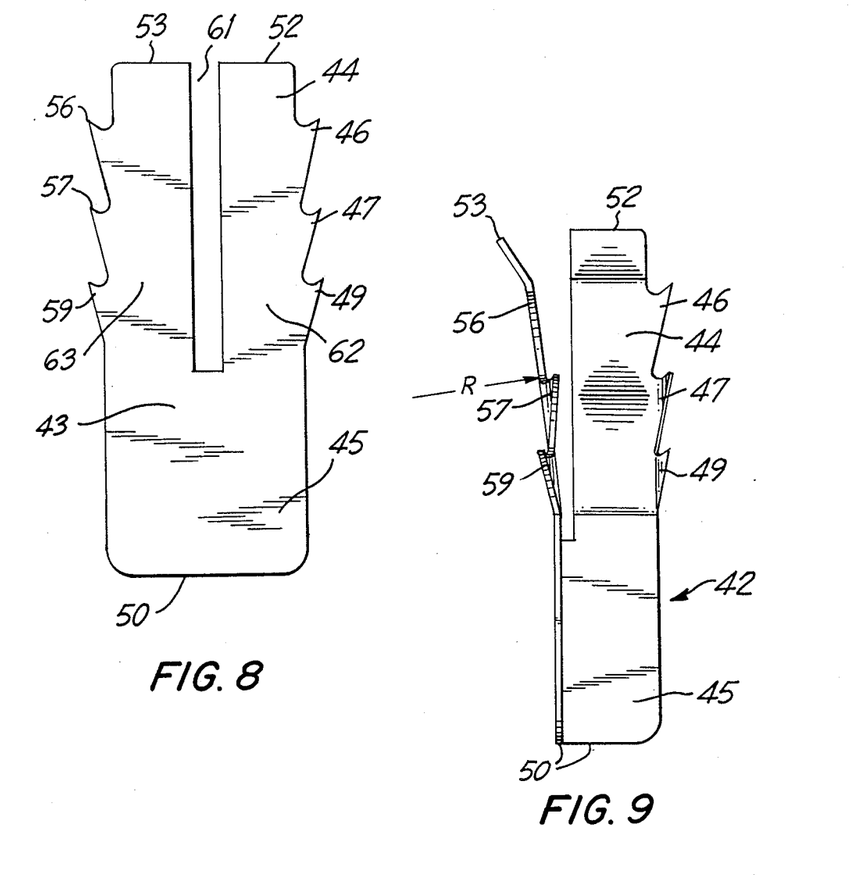
FIG. 8 is an enlarged top plan view of the locking element blank illustrating details of the locking element before forming.
FIG. 9 is a side elevation view of the locking element of the instant invention before assembly into the single use syringe assembly of the instant invention.
Figure 10:
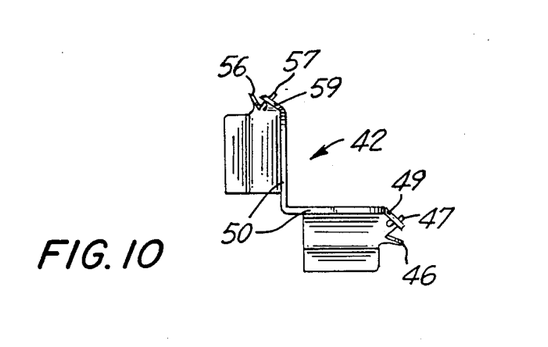
FIG. 10 is a side elevation view of the end of the locking element of FIG. 9.

Locking element 42 is preferably formed of planar sheet material 43 which is preferably harder than the material of the barrel and the plunger rod such as metal.

It is preferred that locking barb 46 remain in the plane of sheet metal 43 while anti twist locking barbs 47 and 49 are positioned at angles with respect to the locking barb preferably with each anti twist locking barb being angled away from the locking barb 46 on different sides of the locking barb as best illustrated in FIG. 10. In any event where anti misuse features are desirable it is preferred that at least two proximally and outwardly facing non parallel locking barbs are provided. If two barbs are used it is preferable that these barbs are included with respect to each other at an angle within the range of about five (5) degrees to ninety (90) degrees.

It is desirable that three barbs are provided with one of the three locking barbs remaining substantially parallel to the body structure or in the plane of the body material, and the other two barbs being bent at angles away from this barb. It is desired but not necessary, if sheet material construction is used for the locking element, that one of the locking barbs should be oriented in the plane of the sheet material. The second locking barb or first anti twist locking barb is preferably located in a plane positioned at an angle of between about five (5) degrees to ninety (90) degrees with respect to the plane of locking barb and the third locking barb or second anti twist locking barb is located in a plane positioned at an angle of between about five (5) degrees and ninety (90) degrees with respect to the plane of the locking barb and preferably oriented toward the opposite side of the plane of the locking barb as the first anti twist locking barb. For the purposes of the present invention the non parallel relationship of the barbs, when the locking element is made of sheet metal, is established by bending one or more of the barbs so that the barbs point in different directions as a result of the barb or barbs being bent.

Locking element 42 also includes a distally and inwardly facing resisting edge 50 and an inwardly facing driving edge 52 at proximal portion 44 of the locking element. For the purpose of describing locking element 42 the term "inwardly" shall mean toward a surface on the plunger rod body portion such as a surface along longitudinal groove 35, and the term "outwardly" shall mean facing generally toward inside surface 22 of barrel 21. Driving edge 52 is adapted to interact with longitudinal recess of the plunger rod to move the locking element along the barrel as the stopper is advanced along the barrel by force applied to the plunger rod. As will be explained in more detail hereinafter, driving edge 52 also, because of its orientation, allows proximal motion of the plunger rod with respect to the barrel during filling while helping to keep the locking element in a fixed position with respect to said barrel. Resisting edge 50 and the locking barbs are adapted to prevent proximal motion of plunger rod 33 with respect to barrel 21 after initial distal motion of the stopper on the plunger rod to expel fluid through passageway 28. Subsequent proximal motion of the plunger rod with respect to the barrel causes resisting edge 50 to engage elongate body portion 34 in the longitudinal recess 35 causing locking element 42 to move in a proximal direction wherein the locking barb 46 engages inside surface 22 of the barrel to prevent further movement and allowing only distal movement of the plunger rod with respect to the barrel.

In this preferred embodiment locking element 42 further includes a second inwardly facing driving edge 53 at proximal portion 44 and a second proximally and outwardly facing locking barb 56 adjacent to additional anti twist locking barbs 57 and 59 which are angularly oriented away from second locking barb 56 and preferably non parallel with respect to each other. Locking barbs 46, 47 and 49 and driving edge 52 are separated from second locking barbs 56, 57 and 59 and second driving edge 53 by longitudinal gap 61 so that driving edge 52 and second driving edge 53 extend proximally in cantilever spring like fashion from distal portion 45 acting to force locking barb 46 and second locking barb 56 against the inside surface of the barrel. As will become more apparent hereinafter it is preferable to have a locking element with spring like qualities such as a locking element formed of metal such as berelium copper or stainless steel with stainless steel sheet metal being preferred for medical applications. It is preferred that the stainless steel sheet metal have a thickness of between about 0.003 inch (0.076 mm) to 0.20 inch (0.508 mm) when used in a syringe barrel having an inside diameter of about 0.333 inch (8.5 mm). Longitudinal gaps 61 divides proximal portion 44 into two cantilever spring arms 62 and 63 which are preferably bent along preferably variable radius R so that the distance across the locking element at the locking barbs is larger than the space available between the plunger rod and the inside surface of the syringe barrel. This configuration requires compression of the spring arms upon assembly and, as will be explained in more detail hereinafter, provides a slight pressure of the locking barbs against the inside surface of the barrel.

The syringe of the present invention may be used with a plurality of locking elements, for example, the preferred embodiment will accept up to four separate locking elements to provide additional mechanical resistance to multiple use. Also, a locking element and/or plunger rod may be shaped so that a single larger locking element engages areas further apart on the inside surface of the syringe barrel such as along 90 degrees to 360 degrees of the inside diameter of a circularly shaped syringe barrel.

An important feature of the instant invention is its ability to provide a syringe assembly having structure for limiting the volume of fluid with which can be taken into the chamber through passageway 28 and subsequently delivered. This feature assists in achieving substantially consistent delivery volumes from syringe to syringe and is useful in programs involving large numbers of subjects being injected with medication at the same time such as immunization programs. This feature also prevents misuse by limiting the volume the syringe assembly is capable of delivering. To limit delivery volume a barrier means such as delivery limiting barrier 65 is provided. Delivery limiting barrier 65 establishes the maximum proximal position of locking element 42 with respect to the elongate body portion of the plunger rod. The barrier function can be accomplished by various structures such as a raised rib positioned transversely along the surface of the plunger rod in the area of the longitudinal recess as will be described hereinafter. As the plunger rod is moved in a proximal direction along the barrel the locking element because of its spring action which forces the locking barbs against the inside surface of the barrel tends not to move with the plunger rod. The delivery limiting barrier provides an obstacle in longitudinal recess 35 over which locking element 42 cannot pass. Accordingly, when the locking element contacts delivery limiting barrier 65 it is forced along the barrel with the plunger rod. The delivery limiting barrier in this embodiment is a circular flange. It is within the purview of the instant invention to include barrier means which is fixed to the plunger rod such as delivery limiting barrier 65 or movable thereon to adjust the volume of the syringe. The instant invention also functions without barrier means wherein the volume chosen is visually determined through use of a graphic scale printed on the syringe barrel (not shown).

Another important feature of the instant invention which helps provide consistently uniform syringe assembly performance throughout production runs of large quantities of syringe assemblies is the inclusion of a ledge such as delivery ledge 67 running transversely across longitudinal recess 35. Delivery ledge 67 includes inclined surface 68 and vertical edge wall 69. Delivery ledge 67 is positioned at a distance which is approximately the overall length of the locking element from the proximal side of the stopper or any structure in the longitudinal recess defining the proximal most limit of the recess, such as support wall 30. Delivery ledge 67 in the preferred embodiment is positioned at a distance of approximately the length of the locking element proximally from support wall 30 so that edge wall 69 is positioned at a distance slightly longer than the length of the locking element from support wall 30. Delivery ledge 67 is lower and less pronounced than the delivery limiting barrier because it is configured to allow the locking element to pass thereover when the locking element moves distally with respect to the plunger rod but to positively engage driving edges 52 and 53 with vertical edge wall 69 when the element moves proximally with respect to the plunger rod. In this preferred embodiment the delivery ledge is formed by a recessed groove in recess 35, however, it is also within the purview of the instant invention to include a delivery ledge formed of a raised projection such as a raised rib.

Initially, the locking element will slide along the longitudinal recess of the plunger rod while air is being forced from the chamber through the passageway in the needle cannula until the locking element abuts against delivery limiting barrier 65. Then the locking element will move with the plunger rod toward the distal end of the syringe barrel. In use, when drawing medication into the chamber through the needle cannula, the plunger rod will move in a proximal direction while the locking element will tend to remain stationary with respect to the barrel until it abuts against support wall 30. This position, as will be explained in more detail hereinafter, defines the maximum volume of the syringe. At this point, medication may be delivered from the syringe by moving the plunger rod in a distal direction with respect to the barrel such as by applying force to disc shaped plunger rod flange 40. As the plunger rod moves toward the distal end of the barrel driving edges 52 and 53 tend to engage the plunger rod surface in the longitudinal recess and travel with the plunger rod. In almost all cases this phenomenon will occur readily because of the higher hardness of the locking element which is forced by its spring action against the plunger rod longitudinal recess. However, to assure that reliable and consistent operation from syringe assembly to syringe assembly delivery ledge 67 through its vertical ledge 69 further facilitates the engagement of driving edges 52 and 53 and the plunger rod longitudinal recess 35. It is desirable to shape the delivery ledge so that portions of the locking element pass readily over it when the locking element moves distally with respect to the plunger rod but to engage the driving edges 52 and 53 when the motion is reversed. To this end delivery ledge 67 is shaped to have inclined surface 68 at its distal side and vertical edge wall 69 at its proximal side. It is also within the purview of this invention to include a delivery ledge which is raised from the surface of the plunger rod longitudinal recess 35 to accomplish the same result.

A tamper resistant barrier 71 is positioned transversely with respect to the plunger rod wall to block access to the locking element through open end 25 of the barrel in order to prevent unwanted tampering with the locking element to defeat the single-use function of the instant invention. It may be possible to use a long instrument such as forceps to reach in and disengage the locking element or to forceably remove it. Tamper resistant barrier 71 acts to prevent this access. In the preferred embodiment, although it is not necessary, the tamper resistant barrier 71 and delivery limiting barrier 65 occupy the same position along the axial length of the plunger rod. A different embodiment of the plunger rod wherein the delivery limiting barrier and the tamper resistant barrier are at separate positions along the plunger rod will be described hereinafter.

Figures 1, 2, 3, 4:
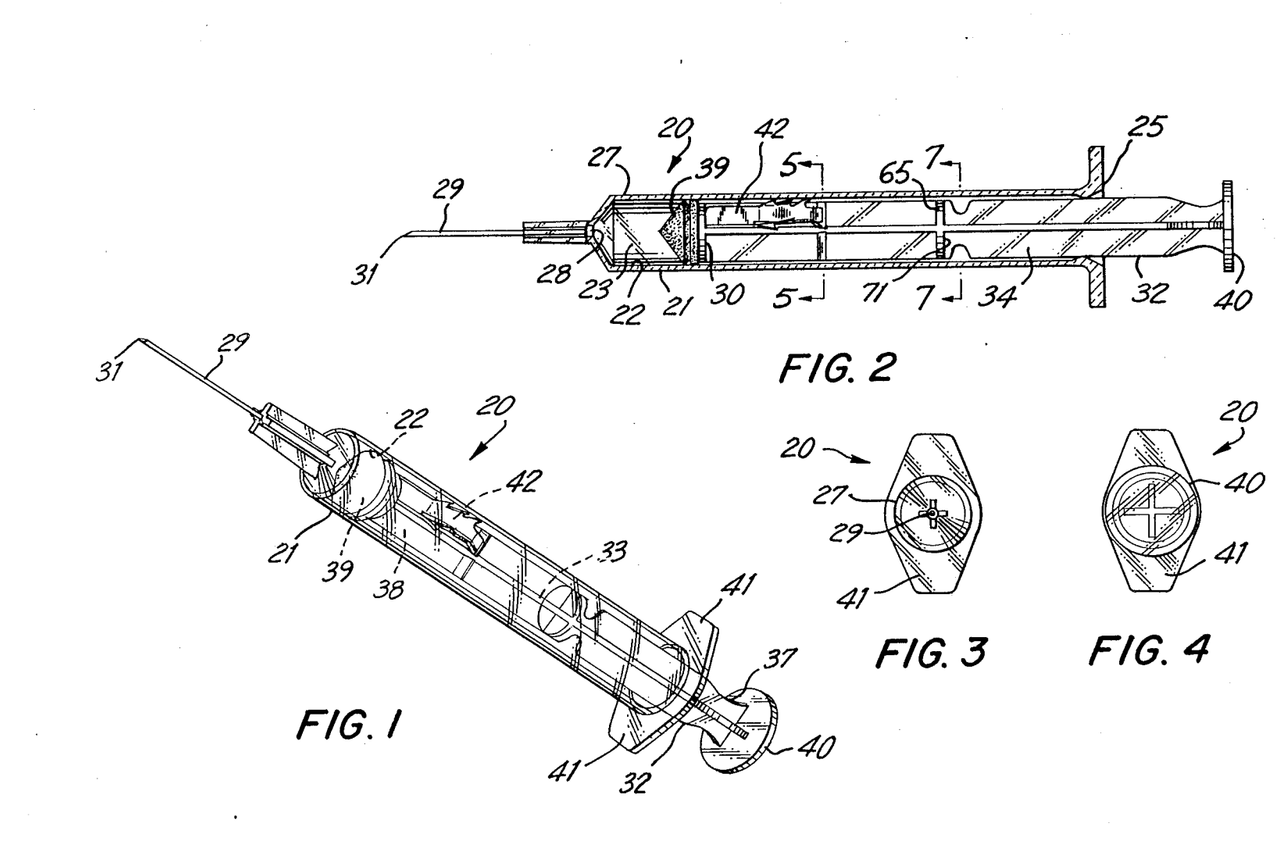
FIG. 1 is a perspective view of the single use syringe assembly of the present invention.
FIG. 2 is a side elevation view of the single use syringe assembly of FIG. 1.
FIG. 3 is a side elevation view of the distal end of the single use syringe assembly of FIG. 2.
FIG. 4 is a side elevation view of the proximal end of the single-use syringe assembly of FIG. 2.
Figure 5:
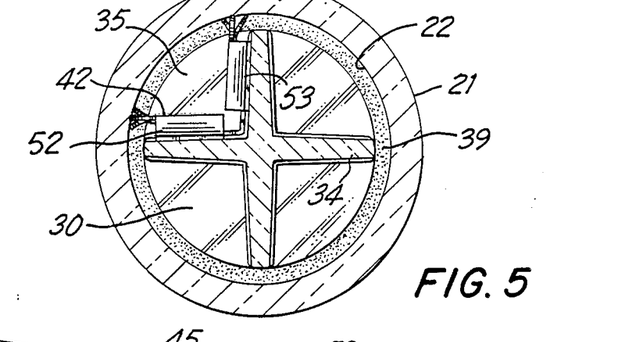
FIG. 5 is an enlarged cross sectional view of the single use syringe of FIG. 2 taken along line 5—5.
Figure 6:
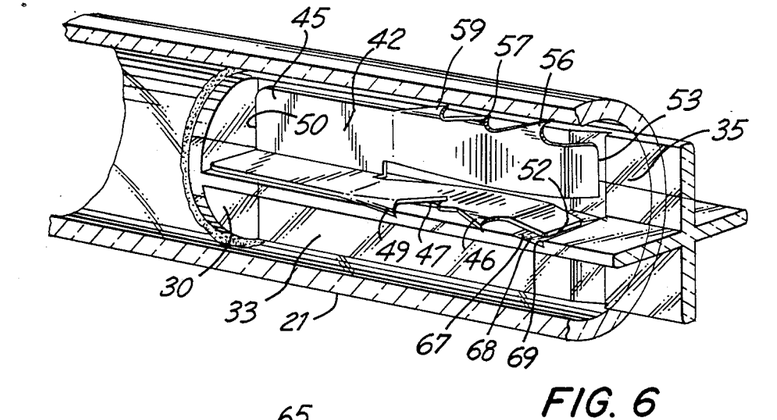
FIG. 6 is an enlarged partial cross sectional perspective view of the portion of the syringe assembly of FIG. 1 containing the locking element.
Figure 7:
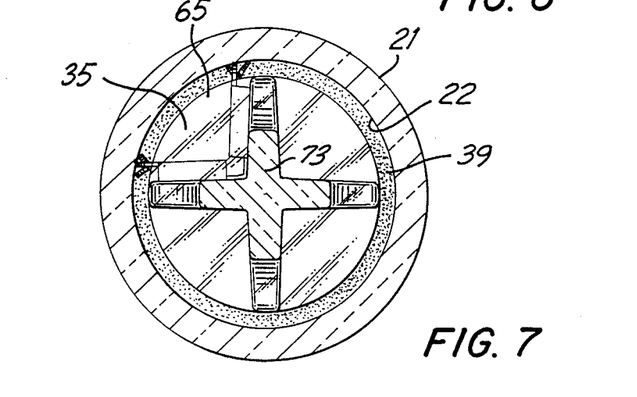
FIG. 7 is an enlarged cross-sectional view of the single use syringe assembly of FIG. 2 taken along line 7—7.

Another feature of the instant invention which helps prevent misuse is the inclusion of a weakening means located between tamper resistant barrier 71 and the proximal end of the plunger rod. In this preferred embodiment the weakening means includes an area of reduced transverse cross-sectional thickness 73, as best illustrated in FIG. 7, which helps to allow the plunger rod to break if excessive an unnecessary amounts of force are applied at the proximal end. A person attempting to defeat the single use function of the instant invention may attempt to do so by twisting or bending the plunger rod in order to distort or defeat the locking element. To avoid this possibility the area of reduced transverse cross sectional thickness in the plunger rod will greatly reduce the resistance of the plunger rod to bending or torsional forces causing it to fail.

To further resist torsional force supplied to the proximal end of the plunger rod and in order to promote failure of the plunger rod at the area of reduced transverse cross sectional, thickness anti-twist locking barbs 47 and 49 and additional anti-twist locking barbs 57 and 59 which are angled out of the plane of locking barbs 46 and 56 respectively are oriented to dig into the syringe barrel wall upon the application of torsional force. For example, anti twist locking barbs 47 and 57 would tend to resist torsional rotation in one direction while anti twist locking barbs 49 and 9 would tend to resist torsional rotation of the plunger rod with respect to the barrel in the opposite direction.

Figure 11:
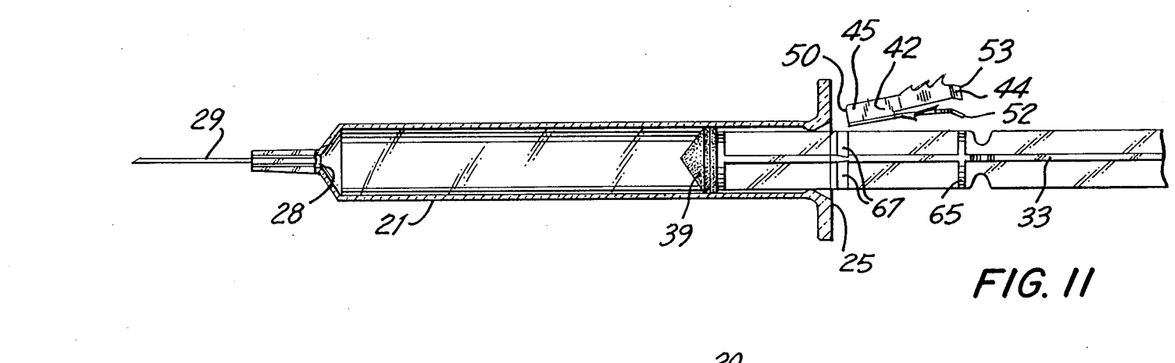
FIGS. 11-14 illustrate the single use syringe assembly of the present invention in use.
Figure 12:
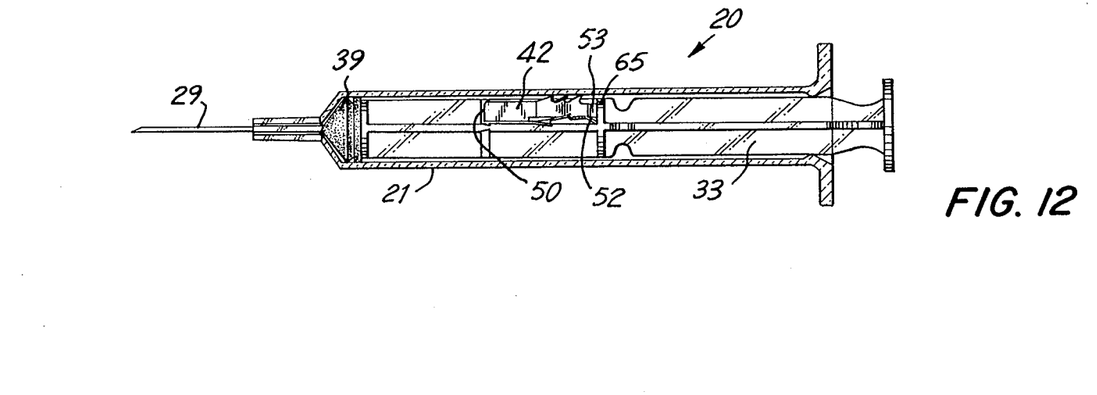
Figure 13:
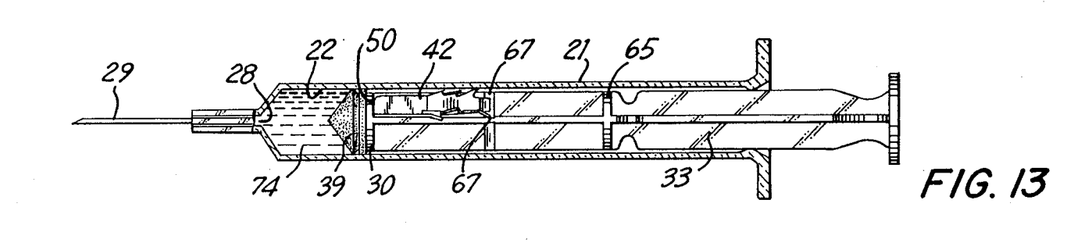

Referring now to FIGS. 11-14 the syringe assembly of the instant invention may be assembled by placing the stopper in the barrel with the plunger rod projecting outwardly from open end 25 of the barrel and then placing locking element 42 in the longitudinal recess in a position which is distal to delivery limiting barrier 65 and then forcing the stopper and plunger rod along the barrel until the stopper is in about its distal most position, as illustrated in FIG. 12. During motion of plunger rod 33 locking element 42 will, because of its spring action and locking barbs, remain substantially in one position with respect to the barrel until driving edges 52 and 53 contact delivery limiting barrier 65 and causes the locking element to move with the plunger rod to the position illustrated in FIG. 12. At this time the syringe needle, if it is not already in fluid communication with a source of medication, may be placed in a stoppered vial containing medication to be injected (not shown) and the plunger rod withdrawn so that medication 74 is drawn into the chamber as best illustrated in FIG. 13. During the step of drawing medication into the chamber the locking element 42 remains in a fixed position with respect to the barrel. This position of the locking element relative to the barrel defines the maximum volume which the syringe assembly will deliver and is established when support wall 30 of the plunger rod contacts resisting edge 50 of the locking element. Further proximal motion of the plunger rod will not occur because the locking element barbs will engage barrel inside surface 22 to resist this motion. The syringe is now ready for administering medication to a patient using known safe procedures. After the medication 74 is expelled from the syringe through passageway 28 and needle cannula 29 the syringe assembly of the instant invention will be in the position illustrated in FIG. 14. While medication is being delivered the locking element will move with the plunger rod along the barrel in a proximal direction because driving edges 52 and 53 are engaging the plunger rod with enough force to prevent any slipping. To facilitate the motion of locking element 42 toward the distal end of the barrel delivery ledge 67 is provided on the preferred embodiment to help improve the engagement between driving edges 52 and 53 and the plunger rod.

Figure 14:
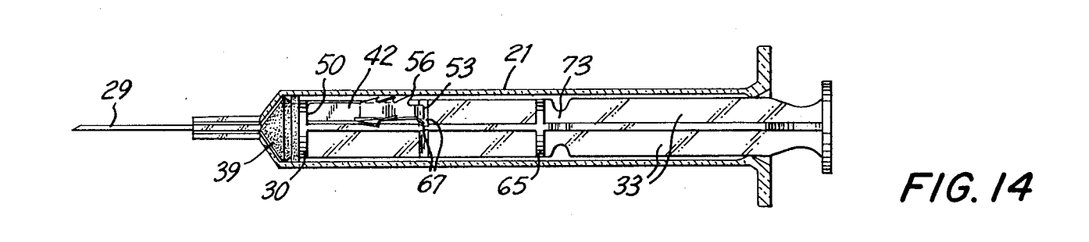

After delivery of the medication stopper 39 and plunger rod 33 are at about their distal most position with respect to barrel 21. Withdrawal of the plunger rod from the barrel may not take place because at this position the proximally and outwardly facing locking barbs are engaging the barrel preventing proximal motion of the locking element with respect to the barrel while the locking element is resisting proximal motion of the plunger rod with respect to the barrel through, in this preferred embodiment, contact between resisting edge 50 of the locking element and support wall 30 of the plunger rod. The syringe of the instant invention has been used once and cannot be used again and can be properly discarded. Any attempt to dislodge the locking element by applying torsional force to the plunger rod will be resisted by the locking element and cause the plunger rod to fracture or break at the area of reduced transverse cross sectional thickness 73. Also, an attempt to subsequently remove or disarm the locking element will be resisted by tamper resistant barrier 71.

It should be noted that the locking element may be placed in the syringe, as illustrated in FIG. 11, during manufacturing and packaged and sterilized while it is in the position illustrated in FIG. 12. In the alternative, the syringe may be packaged and sterilized in a position when the stopper is positioned a distance from the distal end of the barrel so that the syringe contains sterile air which may be used to pressurize the stoppered vial containing medication before drawing medication into the chamber, using known safe procedures.

Figure 15:
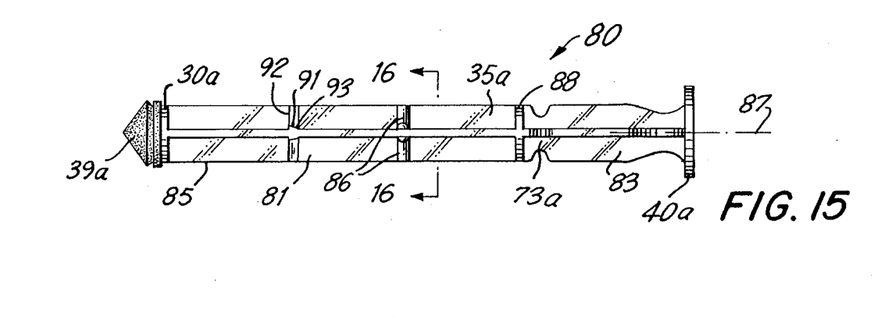
FIG. 15 is a side elevation view of an alternative plunger rod assembly for use in the instant invention.
Figure 16:
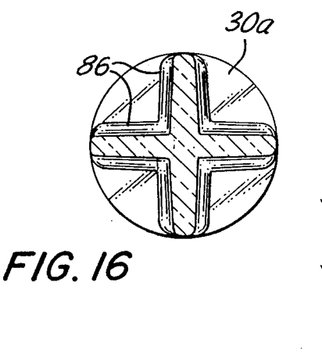
FIG. 16 is a cross sectional view of the plunger rod assembly of FIG. 15 taken along lines 16—16.

Adverting now to FIGS. 15 and 16, an alternative embodiment of the plunger rod and stopper of the instant invention is illustrated. In this alternative embodiment the structure of the plunger rod and stopper is substantially similar to the plunger rod and stopper of the embodiment of FIGS. 1–10. Accordingly, substantially similar components that perform substantially similar functions will be numbered identically to those components of the embodiment of FIGS. 1–10 except a suffix "a" will be used to identify these components in FIGS. 15 and 16. In this embodiment the barrel and locking element although not shown are identical to the embodiment of FIGS. 1–10. In this embodiment an alternative plunger rod and stopper assembly 80 includes a plunger rod 81 having a proximal end 83 and a distal end 85. A stopper 39a at distal end 85 is slidably positioned in fluid tight engagement in the barrel (not shown). Plunger rod 81 includes barrier means on the body portion for limiting the delivery volume of the syringe assembly by establishing the maximum proximal position of the locking element (not shown) with respect to elongate body portion 82 of the plunger rod. In this embodiment barrier means includes raised rib 86 running transversely across longitudinal recess 35a of elongate body portion 82. The plunger rod also includes stopper support means including support wall 30a adjacent to stopper 39a for supporting the stopper during distal motion of the stopper with respect to the barrel. Support wall 30a, in this embodiment, is a support flange positioned transversely with respect to longitudinal axis 87 of elongate body portion 82. The plunger rod also includes tamper resistant barrier 88 in the shape of a barrier flange positioned transversely with respect to longitudinal axis 87. An area of reduced transverse cross sectional thickness 73a is also provided in a position which is proximal to tamper resistant barrier 88 for allowing twisting failure of the plunger rod on application of excessive force to proximal end 83 of the plunger rod. Plunger rod 81 also includes delivery ledge 91 in the form of a raised projection running transversely along longitudinal recess 35a. Delivery ledge 91 includes inclined surface 92 and vertical edge wall 93. Delivery ledge 91 in this embodiment is positioned so that the distance between support wall 30a and vertical edge wall 93 is slightly larger than the length of the locking element (not shown). As with the embodiment of FIGS. 1–10, the positioning of the delivery ledge is determined by the distance between the support wall and the vertical edge wall.

The syringe barrel of the present invention may be constructed of a wide variety of rigid materials with thermoplastic materials such as polypropylene and polyethylene being preferred. Similarly thermoplastic materials such as polypropylene, polyethylene and polystyrene are preferred for the plunger rod. A wide variety of materials such as natural rubber, synthetic rubber and thermoplastic elastomers are suitable for the stopper. The choice of stopper material will depend on compatability with the medication being used. In the preferred embodiment of this invention the stopper, made of medical grade rubber, includes a partially hollow interior with an undercut ledge which is snap fit over a complementary structure on the plunger rod to secure the stopper to the plunger rod. A stopper and plunger rod may also be integrally formed of the same material or of different materials.

As previously recited, it is preferable that the locking element being fabricated from a material which is harder than the barrel and plunger rod material so that the locking barbs and resisting edge and driving edge may effectively engage these components. Resilient spring like properties are also desirable along with low cost dimensionally consistent fabrication. With this in mind, sheet metal is the preferred material for the locking element with stainless steel being preferred for medical applications. Although the locking element of the preferred embodiment is fabricated from a single sheet, it is within the purview of the instant invention to include locking elements made of other forms of material such as wire and locking elements containing multiple parts and apparatus such as hinges and springs to achieve the function of the preferred locking element.

Thus, it can be seen that the present invention provides a simple, straight forward, reliable, easily fabricated, single use syringe having features such as: barrier means for establishing syringe delivery volume; a delivery ledge for more precise interaction of the single use syringe assembly elements; and various features such as non parallel locking barbs, tamper resistant barrier means on the plunger rod, and an area of reduced transverse cross sectional thickness on the plunger rod to help prevent misuse. The present invention provides a single use syringe which becomes inoperable or incapable of further use without any additional act on the part of the user.

What is claimed is:

1. A single-use syringe assembly having misuse resistant features comprising:

a barrel having an inside surface describing a chamber for retaining fluid, said barrel having an open barrel end and a distal barrel end having a passageway therethrough in fluid communication with said chamber;

a plunger rod including an elongate body portion having a proximal end and a distal end, and a stopper at said distal end, said stopper being slidably positioned in fluid tight engagement in said barrel, said body portion extending outwardly from said open barrel end; and a locking element positioned in said barrel between said elongate body portion of said plunger rod and said inside surface of said barrel, said element having a proximal portion and a distal portion, said locking element including at least two adjacent proximally and outwardly facing non parallel locking barbs, a distally and inwardly facing resisting edge and an inwardly facing driving edge at said proximally and outwardly facing non-parallel lock- adapted to interact with said body portion of said plunger rod to move said locking element along said barrel as said stopper is advanced along said barrel, said resisting edge and said barbs adapted to prevent proximal motion of said plunger rod with respect to said barrel after initial distal motion of said stopper to expel fluid through said passageway wherein subsequent proximal motion of said plunger rod with respect to said barrel causes said resisting edge to engage said plunger rod causing said locking element to move in a proximal direction wherein said locking barbs engage said inside surface of said barrel to prevent further movement and allowing only distal movement of said plunger rod with respect to said barrel.

2. The syringe assembly of claim 1 wherein said elongate body portion includes a longitudinal recess, said recess acting as a pathway for the longitudinal motion of said locking element relative to said elongate body portion between said stopper and said barrier means.

3. The syringe assembly of claim 2 wherein said longitudinal recess is v-shaped when viewed along the longitudinal axis of said body portion with the narrowest portion of said recess being closest to the center of the body portion.

4. The syringe assembly of claim 1 wherein at least two of said barbs are inclined with respect to each other at an angle within the range of about 50 degrees to 90 degrees.

5. The syringe assembly of claim 1 wherein said locking element includes an additional second group of at least two adjacent non-parallel proximally and outwardly facing locking barbs and a second inwardly facing driving edge at said proximal portion of said element.

6. The syringe assembly of claim 5 wherein said driving edge and said second driving edge are separated by a longitudinal gap in said element so that said driving edge and said second driving edge extend proximally in cantilever spring like fashion from said distal portion of said element forcing said locking barbs and said second group of locking barbs against said inside surface of said barrel.

7. The syringe assembly of claim 1 wherein said locking element is made of metal.

8. The syringe assembly of claim 1 wherein said locking member is made of sheet metal.

9. The syringe assembly of claim 1 wherein said locking element is made of sheet material wherein one of said locking barbs is oriented in the plane of said sheet material.

10. The syringe assembly of claim 1 wherein one of said non parallel locking barbs is located in a plane positioned at an angle of between 5 degrees to 90 degrees with respect to the plane of the other of said locking barbs.

11. The syringe assembly of claim 10 having an additional locking barb located in a plane positioned at an angle of between 5 degrees and 90 degrees with respect to the plane of one of said non parallel locking barbs.

12. The syringe assembly of claim 1 further including tamper resisting barrier means on said body portion located proximally of the intended path of said locking element along said body portion.

13. The syringe assembly of claim 12 wherein said tamper resistant barrier means is a barrier flange positioned transversely with respect to the longitudinal axis of said body portion.

14. The syringe assembly of claim 13 wherein said barrier flange is circularly shaped.

15. The syringe assembly of claim 12 wherein said body portion and said barrier means are integrally formed of the same material.

16. The syringe assembly of claim 12 wherein said body portion of said plunger rod includes weakening means located proximally of said barrier means for allowing twisting failure of said plunger rod upon application of excessive torsional force to said proximal end of said body portion, said weakening means including an area of reduced transverse cross sectional thickness.

17. The syringe assembly of claim 1 wherein said barrel is made of thermoplastic material.

18. An operable syringe assembly comprising:
a barrel having an inside surface describing a chamber for retaining fluid, said barrel having an open proximal end and a distal barrel end having a passageway therethrough in fluid communication with said chamber;

a plunger rod having an elongate body portion, a proximal end, and a distal end;

a stopper at said distal end, said stopper being slidably positioned in fluid-tight engagement in said barrel; and a locking element positioned in said barrel between said elongate body portion of said plunger rod and said inside surface of said barrel, said locking element including at least two adjacent proximally and outwardly facing non parallel locking barbs, a distally and inwardly facing resisting edge and an inwardly facing driving edge, said driving edge adapted to interact with said body portion of said plunger rod to move said locking element along said barrel as said stopper is advanced distally along said barrel, said resisting edge and said barbs adapted to prevent proximal motion of said plunger rod with respect to said barrel after initial distal motion of said stopper to expel fluid through said passageway wherein proximal motion of said plunger rod with respect to said barrel causes said resisting edge to engage said plunger rod causing said locking element to move in a proximal direction wherein said locking barbs engage said inside surface of said barrel to prevent further movement and allowing only distal movement of said plunger rod with respect to said barrel.

19. A single use misuse resistant syringe assembly having features comprising:
- a plastic barrel having an inside surface describing a chamber for retaining fluid, said barrel having an open proximal end and a distal barrel end having a passageway therethrough in fluid communication with said chamber;
- a plunger rod including an elongate body portion having a longitudinal recess, a proximal end, and a distal end, and a stopper at said distal end, said stopper being slidably positioned in fluid tight engagement in said barrel, said body portion extending outwardly from s id open proximal end of said barrel;
- a metal locking element positioned in said barrel between said longitudinal recess of said plunger rod and said inside surface of said barrel said recess acting as a pathway for the longitudinal motion of said locking element relative to said elongate body portion, said element having a proximal portion and a distal portion, said locking element including at least two adjacent proximally and outwardly facing non parallel locking barbs, a distally and inwardly facing resisting edge and an inwardly facing driving edge at said proximal portion of said element, said driving edge adapted to interact with said longitudinal recess of said plunger rod to move said locking element along said barrel as said stopper is advanced distally along said barrel by force applied to said plunger rod, said resisting edge and said barbs adapted to prevent proximal motion of said plunger rod with respect to said barrel after initial distal motion of said stopper to expel fluid through said passageway wherein subsequent proximal motion of said plunger rod with respect to said barrel causes said resisting edge to engage said longitudinal recess causing said locking element to move in a proximal direction wherein said locking barbs engage said inside surface of said barrel to prevent further movement and allowing only distal movement of said plunger rod with respect to said barrel; and
- tamper resistant barrier means on said body portion located proximally of the intended path of said locking element along said longitudinal recess.

20. The syringe assembly of claim 19 wherein said locking element includes an additional second group of at least two adjacent non-parallel proximally and outwardly facing locking barbs and a second inwardly facing driving edge at said proximal portion of said element.

21. The syringe assembly of claim 20 wherein said driving edge and said second driving edge are separated by a longitudinal gap in said element so that said driving edge and said second driving edge extend proximally in cantilever spring like fashion from said distal portion of said element forcing said locking barbs and said second group of locking barbs against said inside surface of said barrel.

22. The syringe assembly of claim 19 wherein said tamper resistant barrier means is barrier flange positioned transversely with respect to the longitudinal axis of said body portion.

23. The syringe assembly of claim 19 wherein said body portion of said plunger rod includes weakening means located proximally of said barrier means for allowing twisting failure of said plunger rod upon application of excessive torsional force to said proximal end of said body portion, said weakening means including an area of reduced transverse cross sectional thickness.

* * * * *

UNITED STATES PATENT AND TRADEMARK OFFICE
CERTIFICATE OF CORRECTION

PATENT NO. : 4,961,728
DATED : October 9, 1990
INVENTOR(S) : Anthony J. Kosinski It is certified that error appears in the above-indentified patent and that said Letters Patent is hereby corrected as shown below:

Claim 1, Col. 13, line 20, "proximally and outwardly facing non-parallel lock-" should be --proximal portion of said element, said driving edge--.

Signed and Sealed this

Eleventh Day of October, 1994

Attest:

BRUCE LEHMAN

*Attesting Officer*     *Commissioner of Patents and Trademarks*